US011529120B2

(12) United States Patent
Belt et al.

(10) Patent No.: US 11,529,120 B2
(45) Date of Patent: Dec. 20, 2022

(54) ULTRASOUND DEVICE CONTACTING

(71) Applicant: KONINKLIJKE PHILIPS N.V., Eindhoven (NL)

(72) Inventors: Harm Jan Willem Belt, Eindhoven (NL); Franciscus Johannes Gerardus Hakkens, Eindhoven (NL); Godefridus Antonius Harks, Eindhoven (NL); Gerardus Henricus Maria Gijsbers, Eindhoven (NL); Kevin Grayson Wickline, Reedsville, PA (US); Lucas Johannes Anna Maria Beckers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 325 days.

(21) Appl. No.: 16/095,422

(22) PCT Filed: Apr. 26, 2017

(86) PCT No.: PCT/EP2017/059907
§ 371 (c)(1),
(2) Date: Oct. 22, 2018

(87) PCT Pub. No.: WO2017/186781
PCT Pub. Date: Nov. 2, 2017

(65) Prior Publication Data
US 2019/0133553 A1 May 9, 2019

Related U.S. Application Data

(60) Provisional application No. 62/327,500, filed on Apr. 26, 2016.

(30) Foreign Application Priority Data

Jul. 28, 2016 (EP) ..................... 16181692

(51) Int. Cl.
A61B 8/00 (2006.01)
B06B 1/02 (2006.01)
(Continued)

(52) U.S. Cl.
CPC ............ *A61B 8/4281* (2013.01); *A61B 8/429* (2013.01); *A61B 8/4218* (2013.01);
(Continued)

(58) Field of Classification Search
CPC ................ A61B 8/4281; A61B 8/4218; A61B 2090/065; A61B 8/546; A61B 8/56;
(Continued)

(56) References Cited

U.S. PATENT DOCUMENTS 4,935,699 A * 6/1990 Boenning ............... G01R 31/08
324/555
5,175,214 A * 12/1992 Takaya ..................... H01B 1/24
252/500
(Continued)

FOREIGN PATENT DOCUMENTS

JP         S61240800 A      10/1986
WO    WO-2014013735 A1 *  1/2014  ........... A61B 8/4494
(Continued)

OTHER PUBLICATIONS

Knite, et al., "Prospective Polymer Composite Materials for Applications in Flexible Tactile Sensors", Contemporary Robotics—Challenges and Solutions, A D Rodi (Ed.), ISBN: 978-953-307-038-4, InTech, 32 pages.
(Continued)

*Primary Examiner* — Joseph M Santos Rodriguez
*Assistant Examiner* — Kaitlyn E Sebastian

(57) ABSTRACT

An ultrasound device (10) is disclosed comprising a transducer arrangement (110) and an acoustically transmissive window (150) over said arrangement, said window com-
(Continued)

prising an elastomer layer (153) having conductive particles dispersed in the elastomer, the elastomer layer having a pressure-sensitive conductivity, the ultrasound device further comprising an electrode arrangement (160) coupled to said elastomer layer and adapted to measure said pressure-sensitive conductivity. An ultrasound system and arrangement including such an ultrasound device are also disclosed.

18 Claims, 8 Drawing Sheets

(51) Int. Cl.
  *B06B 1/06* (2006.01)
  *G10K 11/02* (2006.01)
  *A61N 7/02* (2006.01)
(52) U.S. Cl.
  CPC ............ *B06B 1/0292* (2013.01); *B06B 1/067* (2013.01); *A61B 8/4488* (2013.01); *A61B 8/546* (2013.01); *A61B 8/56* (2013.01); *A61N 7/02* (2013.01); *B06B 2201/76* (2013.01)
(58) Field of Classification Search
  CPC ..... A61B 8/4488; B06B 1/0292; B06B 1/067; B06B 2201/76; G10K 11/02; A61N 7/02
  See application file for complete search history.

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |
| 6,283,919 B1 | 9/2001 | Roundhill et al. | |
| 6,328,697 B1 | 12/2001 | Fraser | |
| 6,443,896 B1 | 9/2002 | Detmer | |
| 6,458,083 B1 | 10/2002 | Jago et al. | |
| 6,511,427 B1 * | 1/2003 | Sliwa, Jr. ............. | A61B 5/4869 600/438 |
| 6,530,885 B1 | 3/2003 | Entrekin et al. | |
| 6,623,432 B2 | 9/2003 | Powers et al. | |
| 8,771,541 B2 | 7/2014 | Miyoshi et al. | |
| 2003/0180508 A1 * | 9/2003 | McArdle ................ | H05K 3/323 428/195.1 |
| 2004/0236223 A1 * | 11/2004 | Barnes ..................... | A61B 8/04 600/459 |
| 2007/0036492 A1 * | 2/2007 | Lee ......................... | G09G 3/001 385/89 |
| 2007/0161903 A1 * | 7/2007 | Yamashita ........... | A61B 8/4483 600/459 |
| 2010/0246332 A1 | 9/2010 | Huang | |
| 2011/0163630 A1 | 7/2011 | Klootwijk et al. | |
| 2012/0086307 A1 * | 4/2012 | Kandori ................ | B06B 1/0292 310/300 |
| 2012/0090408 A1 | 4/2012 | Jheng et al. | |
| 2012/0194107 A1 * | 8/2012 | Kandori ................ | B06B 1/0246 318/116 |
| 2014/0312737 A1 * | 10/2014 | Jenninger ............... | H01L 41/27 310/319 |
| 2015/0064675 A1 * | 3/2015 | Eichhorn ............... | A61B 34/76 434/262 |
| 2015/0162851 A1 | 6/2015 | Kolltwkijk et al. | |

FOREIGN PATENT DOCUMENTS

| | | | |
|---|---|---|---|
| WO | 2015044827 A1 | 4/2015 | |
| WO | WO-2015044827 A1 * | 4/2015 | ............. A61B 8/145 |

OTHER PUBLICATIONS

Wang et al, "Thin Flexible Pressure Sensor Array Based on Carbon Black/Silicone Rubber Nanocomposite" IEEE Sensors Journal, vol. 9, No. 9, Sep. 2009, pp. 1130-1135.

Grewe et al, Acoustic Properties of Particle Polymer Composites for Ultrasonic Transducer Backing Applications: IEEE Transactions on Ultrasonics . . . , vol. 37, No. 6, Nov. 1190, pp. 506-514.

International Search Report and Written Opinion for International Application No. PCT/EP2017/059907, dated Jul. 7, 2017, 14 pages.

* cited by examiner

ULTRASOUND DEVICE CONTACTING

This application is the U.S. National Phase application under 35 U.S.C. § 371 of International Application No. PCT/EP2017/059907 filed on Apr. 26, 2017, which claims the benefit of U.S. Provisional Application Ser. No. 62/327,500 filed Apr. 26, 2016 and EP Application Serial No. 16181692.1 filed Jul. 28, 2016. These applications are hereby incorporated by reference herein.

FIELD OF THE INVENTION

The present invention relates to an ultrasound device comprising a transducer arrangement.

The present invention further relates to an ultrasound system comprising such an ultrasound device.

The present invention yet further relates to an ultrasound arrangement comprising such an ultrasound device.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the deceased tissue by coagulative necrosis.

Such applications face several challenges. For instance, in imaging applications it is far from trivial to achieve a good contact between the ultrasound transducer array and the part of the body to be imaged. This is typically achieved by using special gels that improve the contact between the ultrasound transducer array and the body part. However, a drawback of this approach is that usually large amounts of gel have to be used, which may contain air bubbles that interfere with the transmission or reception of the ultrasound signals. Moreover, the ultrasound transducer array, e.g. in the form of the probe, is typically hand-held during an imaging procedure, which makes the procedure prone to errors.

Similar challenges exist in therapeutic applications, where the focused beam requires periodic readjustment to treat multiple regions of the diseased tissue. This may be done manually by adjusting a focusing element tile or by beam steering by adjustment of the relative phases of the signals generated by the respective ultrasound transducer elements. The manual adjustment is prone to inaccuracies and the range of phase controlled beam steering may not be sufficient to reach all diseased tissue without array displacement.

There exists a need to assess the quality of the contact between the ultrasound transducer array and a body to be subjected to the ultrasound waves produced with the ultrasound transducer array, such that suboptimal operation of the ultrasound device due to a poor quality conformal contact between the ultrasound transducer array and the body can be avoided or rectified. This for example applies to large area ultrasound transducers and transesophageal echocardiogram (TEE) probes, where it is notoriously difficult to establish a good contact between the ultrasound transducers and the body region to be imaged or treated.

SUMMARY OF THE INVENTION

The present invention seeks to provide an ultrasound device comprising a transducer arrangement capable of assessing the quality of the contact between the transducer arrangement and a body to be subjected to the ultrasound waves produced with the transducer arrangement.

The present invention further seeks to provide an ultrasound system including such an ultrasound device, in which the ultrasound system is adapted to adjust its mode of operation in response to a quality assessment of the contact between the transducer arrangement and a body to be subjected to the ultrasound waves produced with the transducer arrangement as provided by the ultrasound device.

The present invention further seeks to provide an ultrasound arrangement including such an ultrasound device, in which the ultrasound arrangement is adapted to alter the contact between the transducer arrangement and a body to be subjected to the ultrasound waves produced with the transducer arrangement in response to a quality assessment of the contact between the transducer arrangement and the body as provided by the ultrasound device.

According to an aspect, there is provided an ultrasound device comprising a transducer arrangement and an acoustically transmissive window over said arrangement, said window comprising an elastomer layer having conductive particles dispersed in the elastomer, the elastomer layer having a pressure-sensitive conductivity, the ultrasound device further comprising an electrode arrangement coupled to said elastomer layer adapted to measure said pressure-sensitive conductivity.

The inclusion of a pressure-sensitive elastomer layer in the acoustically transmissive window over the transducer arrangement makes it possible to determine the quality of the contact between the ultrasound device and a body to be subjected to the ultrasound waves produced by the ultrasound device, as the conductivity of the elastomer layer as formed by conductive particles in contact with each other is a function of the applied pressure to the layer. Consequently, this conductivity can be measured with the electrode arrangement and can be used as an indicator of the quality of the contact between the ultrasound device and the body.

The elastomer layer preferably has an acoustic impedance that is matched to the acoustic impedance of a body to be exposed to the ultrasound waves produced by the ultrasound device and/or to the acoustic impedance of the transducer arrangement. This ensures an efficient acoustic coupling between the elastomer layer and the body and/or transducer arrangement, thereby minimizing losses of ultrasound waves, e.g. through reflection.

In an embodiment, the acoustic impedance of the elastomer layer is in the range of 1.3-3.0 MRayls, preferably wherein the acoustic impedance is in the range of 1.3-1.9 MRayls. This for example makes the elastomer layer particularly suited for use with e.g. piezoelectric transducer elements and capacitive micro-machined ultrasonic transducer CMUT) elements, with the latter transducer elements being particularly well-matched to a elastomer layer having an acoustic impedance in the range of 1.3-1.9 MRayls.

The transducer arrangement is typically adapted to generate ultrasound waves having a minimum wavelength in a body to be exposed to the ultrasound waves produced. Preferably, the conductive particles having a maximum diameter of less than 10% of said minimum wavelength in order to minimize reflections or scattering of the ultrasound waves by the conductive particles.

The elastomer may be a polyolefin, a diene polymer or a polysiloxane, a co-polymer or block-copolymer comprising a polyolefin, a diene polymer or a polysiloxane or a blend thereof, preferably wherein the elastomer is polybutadiene or polydimethylsiloxane. Such elastomers exhibit the desired elastomer properties at the typical temperatures at which the body is exposed to the ultrasound waves, e.g. at room temperature or body temperature of the patient's body, as well as exhibit acoustic impedances that can be tuned by the inclusion of conductive particles to achieve a desirable acoustic impedance below the percolation threshold of the elastomer.

The conductive particles may be any suitable type of conductive particles such as carbon particles, carbon composite particles, ceramic particles, metal particles, metal alloy particles, composite metal particles and conductive metal oxide particles or combinations thereof. The conductive particles or a combination of conductive particles may be selected on the basis of the desired acoustic functionality of the pressure-sensitive elastomer layer, e.g. to tune the acoustic impedance of the pressure-sensitive elastomer layer.

In an embodiment, the elastomer layer comprises a mixture of electrically conductive particles and non-conductive particles. The inclusion of non-conductive (electrically insulating) particles may facilitate an increase in the acoustic impedance of the elastomer layer.

In an embodiment, the volume of the conductive particles in the elastomer layer is at least 15% by volume based on the total volume of the elastomer layer. It has been found that regardless of the nature of the conductive particles, the elastomer layers according to embodiments of the present invention have good pressure sensitivity if the amount of conductive particles in the elastomer layer is at least 15% by volume but below the percolation threshold of the elastomer layer for an elastomer layer in which conductive paths are formed by applying pressure to the elastomer layer or above the percolation threshold of the elastomer layer for an elastomer layer in which conductive paths are broken by applying pressure to the elastomer layer.

The elastomer layer may have a thickness in the range of 10-200 μm in at least some of the embodiments. It has been found that an elastomer layer having a thickness in this range exhibits a strong conductive response to applied pressure whilst at the same time causing minimal losses of ultrasound waves transmitted by the transducer arrangement through the acoustically transmissive window. In an embodiment, the elastomer layer may form part of an impedance matching layer and may be implemented as a $\lambda/4$ layer in which $\lambda$ is the wavelength of the ultrasound waves travelling through the elastomer layer. Depending of the typical wavelengths of the applied ultrasound waves, such an elastomer layer may have a thickness in the range of 10-100 μm.

In some embodiments, the elastomer layer is sandwiched in between the electrode arrangement. In a particularly advantageous embodiment, the electrode arrangement comprises an electrode matrix arranged to measure the pressure-sensitive conductivity of individual portions of the elastomer layer. In this embodiment, particularly fine-grained information regarding the quality of the contact between the ultrasound device and the body to be exposed to the ultrasound waves can be obtained, due to the fact that for each electrode cell of the electrode matrix such contact information may be independently obtained. The elastomer layer may be a continuous layer or may be a patterned layer in this embodiment, with the patterned layer comprising a plurality of elastomer layer portions, each of said portions being arranged within one of the cells of the electrode matrix.

The acoustically transmissive window may further comprise a further elastomer layer having electrically conductive particles and optionally electrically insulating particles dispersed therein, the elastomer layer having a temperature-sensitive electrical conductivity, the ultrasound device further comprising a further electrode arrangement coupled to said further elastomer layer adapted to measure said temperature-sensitive conductivity. Such a further elastomer layer may be independently optimized to provide temperature information in addition to the pressure information provided by the elastomer layer. Such temperature information for example may be used to measure the quality of the contact between the ultrasound device and the patient's body and/or to prevent overheating of the ultrasound device.

According to another aspect, there is provided an ultrasound system comprising the ultrasound device according to any of the described embodiments, the ultrasound system further comprising a power supply adapted to drive the transducer arrangement of the ultrasound device, wherein the power supply is responsive to the electrode arrangement and adapted to disable the transducer arrangement upon a signal from the electrode arrangement indicative of a change in resistivity of the elastomer layer. Such an ultrasound system may disable the power supply to the transducer arrangement upon an indication derived from the change in resistivity of the elastomer layer that the quality of the contact between the transducer arrangement and the body to be subjected to the ultrasound waves produced by the transducer arrangement has deteriorated, e.g. fallen below a defined quality threshold. By disabling the power to the transducer arrangement, the generation of ultrasound waves by the transducer arrangement under such poor contact conditions is avoided, which is beneficial in terms of extending the lifetime of the ultrasound device as well as in terms of avoiding exposure of unintended areas of the body to such ultrasound waves.

In case the ultrasound device further comprises the aforementioned temperature sensitive further elastomer layer, the power supply may be further responsive to the further electrode arrangement and adapted to reduce the power supplied to or disable the transducer arrangement upon a further signal from the further electrode arrangement indicative of a change in resistivity of the further elastomer layer, e.g. a further signal indicative of the temperature in the further elastomer layer exceeding a critical threshold.

In a particularly relevant embodiment, the transducer arrangement comprises a plurality of capacitive micromachined ultrasonic transducers, each transducer comprising a membrane over a substrate, the membrane and the substrate delimiting a cavity; a first electrode on the substrate separated from the cavity by a first electrically insulating layer; and a second electrode supported by the membrane opposite the first electrode; wherein the power supply is adapted to provide the first electrodes and the second electrodes of the respective capacitive micromachined ultrasound transducers with a bias voltage that forces the membranes of selected capacitive micromachined ultrasound transducers into a collapsed mode; and an alternating voltage on top of the bias voltage that forces the membranes in the collapsed mode to resonate. In this embodiment, operation of the CMUT elements in the so-called collapse mode is avoided when the quality of the contact between the transducer arrangement and the body to be exposed to the ultrasound waves generated by the transducer arrangement is insufficient or when the ultrasound device is at risk of overheating. As it is well-known per se that operation of CMUT elements in the so-called collapse mode enhances the acoustic capabilities of the transducer array at the cost of reduced lifetime of the CMUT elements, the ability to (temporarily) disable the power supply to such CMUT elements where the generation of ultrasound waves with such CMUT elements would not yield the desired result due to the poor quality contact between the transducer array and the body (or where the transducer elements risk being damaged by overheating) is particularly advantageous in this embodiment as it results in an elongated lifetime of the CMUT elements.

According to yet another aspect, there is provided an ultrasound arrangement comprising the ultrasound device of any of the described embodiments and a holder adapted to hold the ultrasound device in an orientation against a body surface to be exposed to ultrasound waves generated with the ultrasound device, the holder comprising an actuator arrangement for adjusting the orientation of the ultrasound device and a controller adapted to control the actuator arrangement, the controller being responsive to a signal provided by the electrode arrangement indicative of a change in resistivity of the elastomer layer. Such an ultrasound arrangement benefits from the fact that the measured resistivity of the elastomer layer can be translated into a quality of contact between the transducer arrangement and the body to be exposed to the ultrasound waves generated by the transducer arrangement, such that the measured resistivity can be used as a feedback signal to control the actuator arrangement such that the ultrasound device is autonomously positioned by the actuator arrangement in an orientation in which the transducer arrangement achieves a good-quality contact with the body to be exposed to the ultrasound waves.

BRIEF DESCRIPTION OF THE DRAWINGS

Embodiments of the invention are described in more detail and by way of non-limiting examples with reference to the accompanying drawings, wherein FIG. 1 schematically depicts an ultrasound device according to an embodiment.

DETAILED DESCRIPTION OF THE EMBODIMENTS

Figure 1:
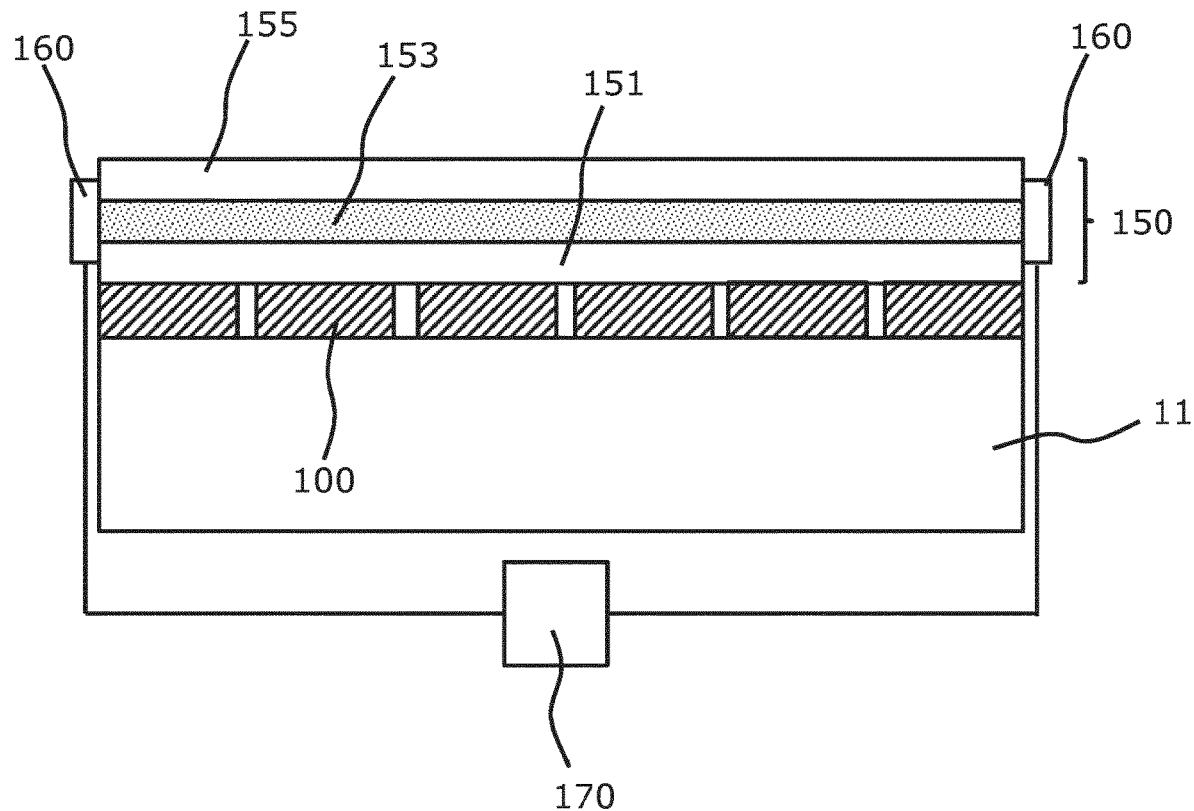

It should be understood that the Figures are merely schematic and are not drawn to scale. It should also be understood that the same reference numerals are used throughout the Figures to indicate the same or similar parts.

In the context of the present application, the term 'conductive' means 'electrically conductive' unless explicitly stated otherwise. Similarly, the term 'non-conductive' means 'electrically insulating' unless explicitly stated otherwise. Where reference is made to an elastomer layer, this is intended to mean a layer of a material or material blend having elastomeric properties and including conductive particles, and optionally further including non-conductive particles. Such particles are typically dispersed in the elastomer layer. FIG. 1 schematically depicts an ultrasound device 10 according to an embodiment. The ultrasound device 10 comprises a plurality of ultrasound transducer tiles 100 on a carrier 11. The plurality of ultrasound transducer tiles 100 will also be referred to as a transducer array. Each tile 100 may comprise one or more ultrasound transducer elements, such as piezoelectric transducer elements or CMUT elements. Alternatively, the ultrasound device 10 may comprise a single crystal transducer element instead of the ultrasound transducer tiles 100. In a particularly preferred embodiment, the ultrasound device 10 comprises a plurality of CMUT tiles 100, wherein the individual CMUT elements on each tile 100 are arranged to be operated in a so-called collapse mode as will be explained in further detail below.

An acoustic window 150 is arranged over the ultrasound transducer tiles 100, i.e. directly or indirectly on the ultrasound transducer tiles 100, such that the ultrasound transducer elements of the transducer array are arranged to transmit ultrasound waves through the acoustic window 150. In other words, the acoustic window 150 is acoustically coupled to the transducer arrangement 160, namely to the transmitting surfaces of the ultrasound transducer elements of the transducer arrangement 160. Such an acoustic window 150 protects the transducer array from being directly contactable, thereby protecting the transducer array from damage, as well as protects the body to be exposed to the ultrasound waves to be generated by the transducer array from being directly contacted by the transducer array, e.g. to protect the body from accidental electrical shock. As is well-known per se, such an acoustic window 150 may further provide impedance matching between the transducer array and the body.

In an embodiment, the acoustic window 150 comprises an elastomer layer 153 having conductive particles dispersed in the elastomer layer to impart pressure-sensitive conductivity onto the elastomer layer 153. The elastomer provides an electrically insulating matrix for the conductive particles. The conductive particles are present in a concentration in the elastomer below the percolation threshold of the elastomer, i.e. below the limit at which the conductive particles form permanent conductive pathways through the elastomer layer 153, i.e. are in permanent contact with each other. Instead, such conductive pathways are temporarily formed by the application of a pressure on the elastomer layer 153, thus causing a change, e.g. a decrease, in the electrical resistance of the elastomer layer 153. A change in the applied pressure to the elastomer layer 153 typically causes a change in the number and/or length of the conductive pathways formed by the conductive particles through the elastomer layer 153, such that a change in pressure applied to the elastomer layer 153 typically causes a change in the electrical resistance of this layer. Therefore, the electrical resistance of the elastomer layer 153 provides an indication of the contact between the transducer array of the ultrasound device 10 and a surface brought into contact with the acoustic window 150, e.g. part of a body of a patient to be exposed to the ultrasound waves generated by the transducer array including the ultrasound transducer tiles 100.

Alternatively, the conductive particles may be present in a concentration in the elastomer above the percolation threshold of the elastomer, i.e. above the limit at which the conductive particles form permanent conductive pathways through the elastomer layer 153, i.e. are in permanent contact with each other. In this embodiment, such conductive pathways are temporarily disrupted by the application of a pressure on the elastomer layer 153, thus causing a change, e.g. an increase, in the electrical resistance of the elastomer layer 153. In order to achieve good pressure sensitivity in the elastomer layer 153, the concentration of the conductive particles in the elastomer layer 153 preferably is at least 15% by volume based on the total volume of the elastomer layer and more preferably is close to the percolation threshold of the elastomer, e.g. below or above the percolation threshold, to maximize piezoelectric sensitivity of the elastomer, e.g. the concentration of the conductive particles in the elastomer layer 153 may be 15-25% by volume based on the total volume of the elastomer layer.

The elastomer layer 153 preferably is acoustically matched to the acoustic impedance of the transducer array, i.e. has an acoustic impedance that approximately matches the acoustic impedance of the transducer array. For example, in case of the transducer array comprising piezoelectric transducers, the elastomer layer 153 may have an acoustic impedance ranging from 1.3-3.0 MRayls, whereas in case of the transducer array comprising CMUT elements, the elastomer layer 153 may have an acoustic impedance ranging from 1.3-1.9 MRayls, which has the further advantage that he acoustic impedance is closely matched to that of body tissue, which typically has acoustic impedance of about 1.6 MRayls. In an example embodiment, the elastomer layer 153 has an acoustic impedance ranging from 1.4-1.7 MRayls.

The acoustic impedance of the elastomer layer 153 may be tuned by selection of the elastomer, i.e. by choosing an elastomer having a suitable intrinsic acoustic impedance, which intrinsic acoustic impedance may be adjusted by the inclusion of conductive particles having a further intrinsic acoustic impedance, such that the overall acoustic impedance of the elastomer layer 153 is defined by the combination of the intrinsic acoustic impedance of the elastomer and the further intrinsic acoustic impedance of the conductive particles. A mixture of conductive particles having different intrinsic acoustic impedances may be used for this purpose.

For example, the acoustic impedance of the elastomer layer 153 may be tuned by selecting conductive particles having a particular density and/or size, as the acoustic impedance Z of the particle may be expressed as $Z=v*d$, in which v is the speed of sound and d is the particle density. Hence, relatively heavy (dense) particles may be used to increase the intrinsic acoustic impedance of the elastomer of the elastomer layer 153.

Any suitable elastomer may be used as the elastomer for the elastomer layer 153. For example, the elastomer may be a polyolefin, a diene polymer or a polysiloxane, a co-polymer or block-copolymer comprising a polyolefin, a diene polymer or a polysiloxane or a blend thereof although embodiments are not limited thereto. Polybutadiene, polydimethylsiloxane and relatively soft polyether block amides (PEBA) commonly used in catheters, are specifically mentioned as suitable elastomers.

Any suitable conductive particle may be used in the elastomer layer 153. For example, the conductive particles may comprise at least one of carbon particles, e.g. graphite or graphene particles, carbon composite particles, ceramic particles, metal particles, metal alloy particles, composite metal particles and conductive metal oxide particles although embodiments are not limited thereto.

In at least some embodiments, the elastomer layer 153 comprises a mixture of conductive particles and non-conductive particles. The inclusion of non-conductive particles may be useful to tune the acoustic impedance of the elastomer layer 153. For example, the non-conductive particles may be particles having a relatively high density such that a small fraction of non-conductive particles relative to the total fraction of particles (i.e. non-conductive particles+conductive particles) in the elastomer layer 153 can significantly increase the acoustic impedance of the elastomer layer 153 without significantly reducing its piezoelectric sensitivity. Any suitable non-conductive particles or mixture of non-conductive particles may be used for this purpose. By way of non-limiting example, the non-conductive particles may be ceramic particles, e.g. transition metal oxide, nitride, carbide particles, high-density metal oxide, nitride, carbide particles and so on.

In an embodiment, the elastomer layer 153 has a thickness in the range of 10-200 μm, e.g. 150 μm. If the thickness of the elastomer layer 153 exceeds 200 μm, the flexibility of the elastomer layer 153 may deteriorate. If the thickness of the elastomer layer 153 is less than 10 μm, it may be difficult to achieve the desired pressure sensitivity in the elastomer layer 153.

In a particular embodiment, the the pressure sensitive elastomer layer 153 may be a matching layer having a thickness of $\lambda/4$ to prevent reflections of ultrasound waves having a wavelength $\lambda$ passing through the elastomer layer 153. For example, the propagation speed v of ultrasound waves through PDMS is 1000 m/sec. For ultrasound waves having a frequency f of 10 MHz, $\lambda=v/f=100$ micron. By choosing the PDMS layer to have a thickness d=25 micron, large scale reflections of the 10 MHz ultrasound waves by the elastomer layer 153 are effectively avoided. From the foregoing, it will be immediately apparent to the skilled person that the thickness d of the elastomer layer 153 may be tuned based on the propagation speed v of ultrasound waves through the elastomer layer 153 as well as based on the major or center frequency f of the ultrasound waves generated by the ultrasound device 10. The ultrasound device 10 may be adapted to generate ultrasound waves in a particular wavelength range in the body of the patient. For example, ultrasound waves in the 7-12 MHz range correspond to a wavelength in the body of about 0.1-0.2 mm. The maximum particle size of the conductive particles in the elastomer layer 153 preferably are chosen in accordance with the wavelength range of the ultrasound waves that the ultrasound device 10 can produce in order to minimize reflection of the ultrasound waves emanating from the transducer array (or of ultrasound echoes returning to the ultrasound device 10). For this reason, the conductive particles and non-conductive particles if present preferably have a maximum diameter of less than 10% of the minimum ultrasound wavelength that can be produced by the ultrasound device 10.

In the context of the present application, the term 'maximum diameter' refers to the maximum cross-sectional dimension of the (non-)conductive particle, and is not intended to limit the shape of the (non-)conductive particles to spherical particles. The (non-) conductive particles may have any suitable shape, e.g. may be spherical, platelets, flakes, nanoparticles including core-shell nanoparticles, nanowires, nanorods, nanotubes and so on.

The ultrasound device 10 further comprises an electrode arrangement 160 conductively coupled to the elastomer layer 153. In FIG. 1, the electrode arrangement 160 is arranged along the periphery of the elastomer layer 153, i.e.

is arranged along at least one edge of the elastomer layer 153. The electrode arrangement 160 is conductively coupled to a sensing circuit 170 arranged to sense the piezoelectric resistivity of the elastomer layer 153. For example, the sensing circuit 170 may be arranged to apply a voltage potential across the elastomer layer 153 with the electrode arrangement 160 and measure the resulting current running through the elastomer layer 153. Alternatively, the sensing circuit 170 may be arranged to apply a current across the elastomer layer 153 with the electrode arrangement 160 and measure the resulting voltage drop across the elastomer layer 153 to determine its resistivity. Other suitable ways of measuring the piezoelectric resistivity of the elastomer layer 153 will be immediately apparent to the skilled person.

The acoustic window 150 may comprise additional acoustically transparent layers. In an embodiment, the acoustic window 150 further comprises an outer layer 155 arranged such that the elastomer layer 153 is arranged between the outer layer 155 and the ultrasound transducer tiles 100. In another embodiment, the acoustic window 150 further comprises an inner layer 151 arranged such that the inner layer 151 is arranged between the elastomer layer 153 and the ultrasound transducer tiles 100. In yet another embodiment, the acoustic window 150 further comprises the inner layer 151 and the outer layer 155 arranged such that the elastomer layer 153 is arranged in between the inner layer 151 and the outer layer 155, as shown in FIG. 1.

The outer layer 155 is intended to face a patient or a body to be examined or treated with the ultrasound device 10. For example, the outer layer 155 may comprise any suitable electrically insulating material such as an electrically insulating polymer, e.g. elastomer, to protect the elastomer layer 153 from damage and to protect the patient from accidental electrical shock during electrical conductivity of the elastomer layer 153. The outer layer 155 for example may comprise a blend of a thermoplastic polymer selected from a polyolefin family (thermoplastic polyolefin or TPO) and an elastomer selected from a polyolefin family (polyolefin elastomer or POE). Elastomers are generally characterized by wide-meshed crosslinking of the "knotted" molecular chains. This type of crosslinking means that the materials have a high level of dimensional stability but are still elastically malleable. By applying load (for instance tensile load) the chains become stretched, but after removal of the load they relax again. A typical hardness of the uncured elastomers is below 50 ShoreA, measured by a durometer (A scale). An olefin family (also alkenes) is a family of the unsaturated hydrocarbons comprising at least one carbon-carbon double bond. A polyolefin is a polymer comprising monomers selected from the olefin family. Most commercially available POEs are copolymers of either ethylene-butene or ethylene-octene.

Thermoplastic polymers are polymers in which, unlike elastomers, the molecular chains are not crosslinked. They consequently demonstrate plastic elastic behavior and are thermoformable (having the property of softening or fusing when heated and of hardening again when cooled). This formability is reversible, in other words can be repeated as often as required as long as the material is not thermally damaged by overheating. Since thermoplastics have little or no cross-linking their individual polymer chains can slip past one another on heating. In thermoplastic polyolefin, compared to the saturated hydrocarbons, the polyolefin family provides the thermoplastic polymer with a relatively light molecular weight, here it is assumed that the thermoplastic polymer does not further contain oxygen comprising functional groups. The thermoplastic polyolefin may comprise linear isotactic polymers. In general thermoplastic polymers have a hardness of above 60 ShoreA.

The introduction of the polyolefin elastomer into the blend of the polyolefin thermoplastic polymer used for the outer layer 155 may provide an increased shear wave attenuation that beneficially reduces crosstalk between the ultrasound transducer elements of the ultrasound transducer tiles 100. Therefore, the acoustic window 150 of the ultrasound device 10 may include an outer layer 155 formed from a blend of the thermoplastic polyolefin and polyolefin elastomer to achieve a reduction of image artifacts during ultrasound imaging.

Blending (compounding) of these polymer materials can, for instance, be performed with a twin screw extruder. The blend of the thermoplastic polymer and the elastomer represents a so called immiscible polymer blends (heterogeneous polymer blends), wherein the blend made of these two polymers exhibits two sets of distinct physical properties, such as glass transition temperatures and melting point, corresponding to the materials forming the blend. An additional advantage of the polyolefin elastomer that it is compatible with most olefinic materials, where in olefinic is any of a class of unsaturated open-chain hydrocarbons having at least one double bond.

An introduction of the polyolefin elastomer into the blend with thermoplastic polyolefin may change the density of the blend compared to the pure thermoplastic, such that the acoustic impedance of the outer layer 155 may be beneficially adjusted to match the acoustic impedance of the elastomer layer 153 and/or the acoustic impedance of soft tissue (which is about 1.6 MRayls). Other acoustic properties of the outer layer, such as acoustic wave velocity, acoustic energy attenuation and shear wave attenuation, may be also tuned by selecting a different ratio of the elastomer content blended in the thermoplastic polymer. It is desirable to use thermoplastic polyolefin at the outer layer 155, which may provide mechanical robustness without compromising ultrasound image quality.

An example material for the thermoplastic polymers used in the outer layer 155 is polymethylpentene (poly 4-methyl pentene-1). Polymethylpentene (available from Mitsui under trade name is TPX) material shows a low longitudinal acoustic attenuation. In this context, the longitudinal attenuation corresponds to the wave's amplitude reduction while propagating from the inner surface of the acoustic window 150 arranged to face the transducer array to the outer surface of the acoustic window 150. In a frequency range from 0 up to 10 MHz, polymethylpentene shows an attenuation value below 3 dB/mm for ultrasound frequencies up to 10 MHz.

In a further example, polymethylpentene may be blended with a copolymer forming the polyolefin elastomer. Copolymers are a physical mix of polymers (two different monomers) which consist of materials with different elastic properties. The copolymer of the polyolefin elastomer is a copolymer of ethylene and alpha olefin such as octane or butane. Alpha-olefins (or α-olefins) are a family of organic compounds which are alkenes with a chemical formula $C_nH_{2n}$, distinguished by having a double bond at the primary or alpha (α) position. In another embodiment, the outer layer comprises a blend of polymethylpentene and ethylene-octene copolymer. This copolymer is available from Dow Chemical under trade name Engage.

Ethylene-octene copolymer is suitable for blending with polymethylpentene due to its olefin nature. This copolymer exhibits on average lower, than the TPX, acoustic impedance and almost an order of magnitude higher shear wave attenuation. The resulting blend of the TPX and ethylene-octene copolymer inherits from the TPX the reduced density with relatively high acoustic wave velocity; and from the copolymer reduced acoustic impedance and increased shear wave attenuation. Therefore, a particularly suitable outer layer 155 comprises a blend of TPX and ethylene-octene copolymer. This blend provides the acoustic window 150 of the ultrasound device 10 with durability and low acoustic attenuation properties next to the improved imaging quality due to the reduced image artifacts originating from the acoustic window 150.

The inner layer 151 may comprise any suitable electrically insulating material such as an electrically insulating polymer, e.g. elastomer, to electrically insulate the transducer array from the elastomer layer 153. The material(s) forming the inner layer 151 may be selected based on the acoustic requirement of the ultrasound transducers, such as their acoustic impedance and mechanism of the electro-acoustical transformation. The inner layer 151 may provide an acoustic coupling of the emitting surface of the ultrasound transducer array to the acoustic window 150.

In order to provide a particularly effective acoustic coupling of the inner layer 151 to the ultrasound transducer tiles 100, in particular to CMUT tiles 100, the inner layer 151 may comprise one or more materials selected from thermoset rubbers. The thermoset rubbers are polymeric materials which may contain only hydrogen and carbon atoms and have a relatively low density (below 1 g/cm$^3$).

For example, the inner layer 151 may comprise polybutadiene or butyl rubber. Butyl rubber is an isobutylene-isoprene copolymer and shows hardness as low as 40 ShoreA. Polybutadiene belongs to the thermoset rubbers containing no other atom types than hydrogen and carbon. This material shows one of the lowest attenuation effects on the propagating acoustic energy. The polybutadiene layer used as materials for the inner layer 151 show an improved acoustic wave transmission (lower attenuation) for the entire acoustic window 150, in particular when the transducer elements are CMUT elements. This may be attributed to the different mechanism of the electro-acoustical transformation in the CMUT compared to the PZT. The PZT-based transducer typically has a parallelepiped shape, wherein at least one of its faces is adapted to vibrate in a piston-like motion during the transmission of the acoustic wave. The displacement of the vibrating (active) face is homogeneous throughout the face surface.

In contrast, the CMUT's vibrating membrane has a different displacement throughout the membrane's area (surface). In a conventional operation mode the membrane's displacement is highest in the central part of the CMUT cell and lowest at the periphery of the membrane. In a collapsed mode of operation, as will be explained in more detail below, the membrane of the CMUT is partially contacting the cell floor, which results in the biggest membrane displacement (D) compared to the conventional operation mode.

The variation in the displacement of the membrane's vibrating portions imposes different requirements on the properties of the inner layer 151 of the acoustic window layer 150 in order to provide an improved acoustic coupling of the operating CMUT elements. The acoustic window 150, in particular the inner layer 151, may need to adopt its inner surface to the membrane's displacement. The relatively light molecular weight of the polybutadiene combined with its relatively low hardness (below 60 ShoreA, preferably below 50 ShoreA) may provide an improved acoustic contact between the acoustic window 150 and the CMUT's membrane adapted to vibrate. In addition the low acoustic wave attenuation of the material forming the inner layer may provide an improved transition of the wave throughout the acoustic window 150.

Polybutadiene has an acoustic impedance of about 1.45 MRayl. In order to minimize an impedance mismatch between the transducer array and the body tissue to be exposed to the ultrasound waves are generated with the transducer array, it may be desirable to increase the acoustic impedance value of the acoustic window material, e.g. the inner layer 151, comprising the polybutadiene, e.g. to about 1.6 MRayl to match the acoustic impedance of soft body tissue. This can be achieved by adding a filler, such as electrically insulating particles, into the inner layer 151. The introduction of the electrically insulating particles into the inner layer 151 increases a total density of this layer. The additional acoustic losses caused by the embedded insulating particles have been found to be sufficiently low and do not considerably influence the quality of the acoustic wave propagation through the acoustic window 150. The acoustic impedance of the layer can be tuned towards higher values, e.g. closer to the tissue's acoustic impedance, while the attenuation of the layer still remains below 1.5 dB/mm for ultrasound frequencies up to 10 MHz, even for inner layers 151 comprising 25% of its weight in the form of the insulating particles (e.g. $ZrO_2$ particles). When the inner layer 151 comprising the polymeric material with embedded insulating particles has a density equal or above 0.94 g/cm$^3$ and an acoustic impedance equal or above 1.5 MRayl, a direct acoustical coupling of the acoustic window 150 to the membrane of the CMUT element is provided. Thus, no additional coupling medium between the acoustic window 150 and the CMUT array is required.

The advantage of the light molecular weight thermoset rubbers is that compared to commonly used in ultrasound silicon based rubbers (filled silicone), these thermoset rubbers, in particular polybutadiene, possess higher acoustic impedance. Therefore, in order to tune the acoustic impedance of the polyolefin based polymeric layer to the body tissue impedance, a relatively small amount of the filler may be needed in this polymeric material, compared to e.g. filled silicones.

In an embodiment, ceramic particles may be used as the electrically insulating particles in the inner layer 151. Ceramic particles, such as metal oxides ($ZrO_2$, $Al_2O_3$, $TiO_2$, $Bi_2O_3$, $BaSO_4$, etc.) show high insulating properties, which may be advantageous in providing additional insulation to the electronics of the ultrasound device 10, e.g. electronics embedded in the carrier 11. The acoustic properties of the inner layer 151 as well as the outer layer 155 may be tuned by varying the weight ratios of the insulating particles embedded in these layers.

However, although the above gives particularly suitable materials for the inner layer 151 and the outer layer 155, it should be understood that embodiments of the present invention are not limited to these particulars suitable materials and that any suitable material may be used for the inner layer 151 and the outer layer 155 respectively. Moreover, the various elastomer materials and material blends described as embodiments of the inner layer 151 and the outer layer 155 equally may be used as the elastomer of the elastomer layer 153.

Figure 2:
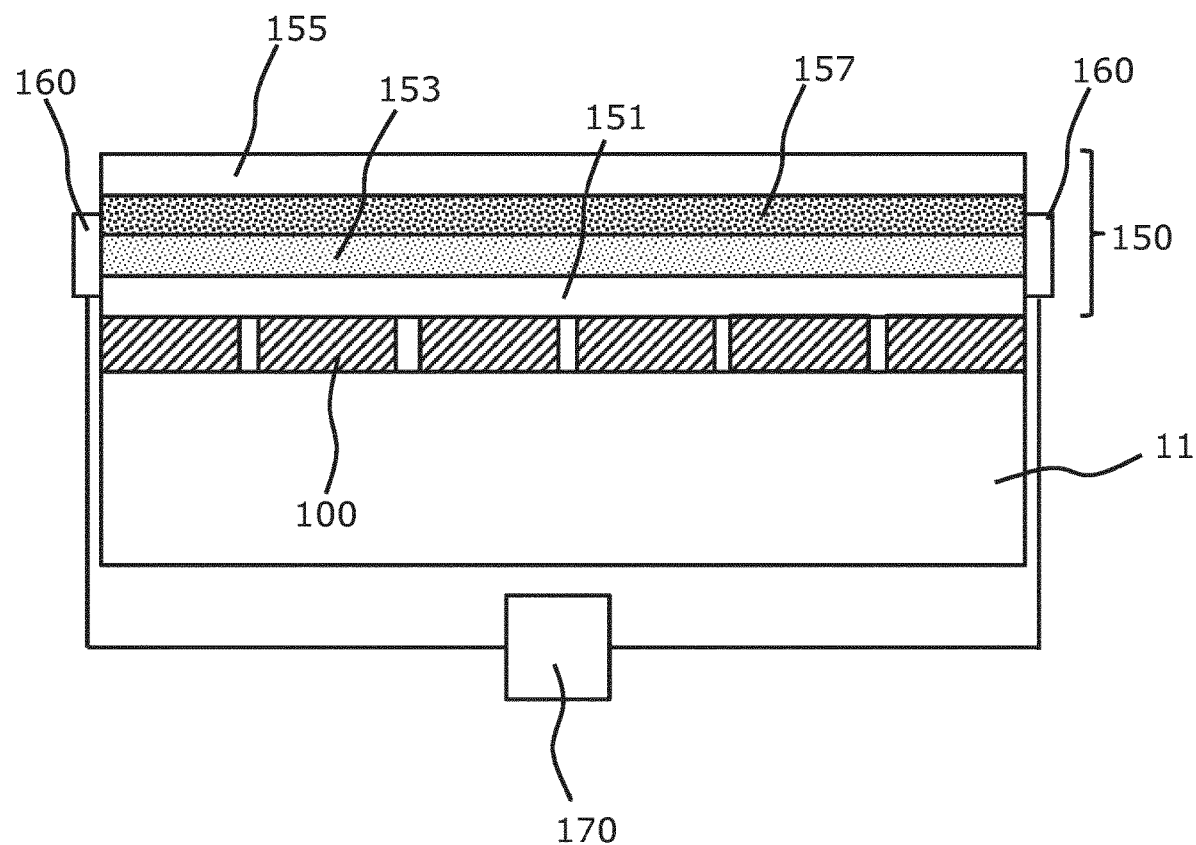
FIG. 2 schematically depicts an ultrasound device according to another embodiment.
Figure 3:
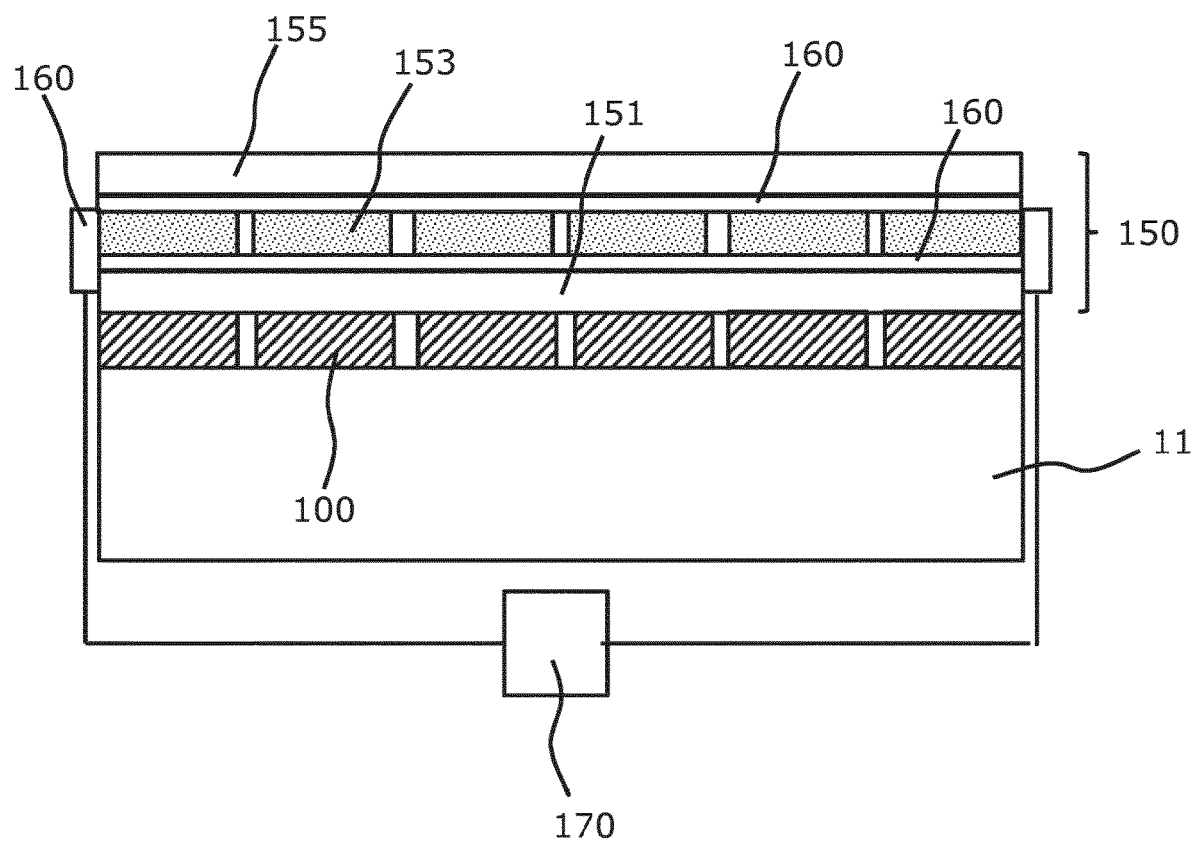
FIG. 3 schematically depicts an ultrasound device according to yet another embodiment.

FIG. 2 schematically depicts another embodiment of an ultrasound device 10. In this embodiment, the elastomer layer 153 is sandwiched between the electrode arrangement 160. Such a sandwiched configuration may increase the sensitivity of the sensing circuit 170 due to a larger contact area between the respective electrodes of the electrode arrangement 160 and the elastomer layer 153. The electrode arrangement 160 may comprise an upper electrode 157 on the elastomer layer 153, e.g. arranged between the elastomer layer 153 and the upper layer 155 and a lower electrode on the elastomer layer 153 opposite the upper electrode 157, e.g. arranged between the elastomer layer 153 and the lower layer 151 of the acoustic window 150. The electrodes of the electrode arrangement 160 may be kept as thin as possible, e.g. less than 1 micron, to minimize interference with the ultrasound waves passing through the electrodes. At such thicknesses, any suitable conductive material may be used for the electrodes, e.g. metal or metal alloy electrodes such as Au, Ni, Ni/Cr, Cu or Cu/Ti electrodes, conductive metal oxide electrodes, e.g. ITO electrodes, conductive polymer or conductive polymer composite electrodes, and so on. Many other electrode materials will be immediately apparent to the skilled person. FIG. 3 schematically depicts yet another embodiment of an ultrasound device 10. Compared to the embodiments schematically depicted in FIG. 2, the electrode arrangement 160 is patterned to form an electrode matrix of individually addressable electrode cells, such that each electrode cell may determine the piezoelectric resistivity of a portion of the elastomer layer 153 between the electrode portions of the cell, i.e. each elastomer layer portion may be individually addressed by the electrode arrangement 160. For example, the electrode arrangement 160 may be implemented as a passive matrix arrangement to facilitate the individual addressing of the respective portions of the elastomer layer 153. In this embodiment, a particularly fine-grained contact pressure map may be created for the transducer array, as the contact quality of each elastomer layer portion with the patient's body may be obtained from interrogation of that particular elastomer layer portion with the electrode arrangement 160.

The electrode matrix may comprise opposing patterned electrodes as well as a patterned electrode opposite a common electrode, e.g. a patterned electrode in between the elastomer layer 153 and the ultrasound transducer tiles 100 and an opposing common electrode or a common electrode in between the elastomer layer 153 and the ultrasound transducer tiles 100 and an opposing patterned electrode. The elastomer layer 153 may be provided as a continuous layer or alternatively may be patterned into a plurality of portions, with each portion being arranged between opposing electrode portions of an electrode cell of the electrode matrix.

In at least some embodiments, the electrode of the electrode arrangement facing the patient's body may be grounded to reduce the risk of electrical shock.

Although not specifically shown in FIG. 1-3, the acoustic window 150 may comprise additional layers, which may be tuned to fulfill a particular function. For example, the acoustic window may further comprise a further elastomer layer comprising further electrically conductive particles and optionally further comprising further non-conductive particles, in which the properties of the further elastomer layer, e.g. the size, shape and/or density of the further electrically conductive particles and optional further non-conductive particles, are tuned to optimize the temperature sensitivity of the further elastomer layer, e.g. by imparting a temperature-dependent resistivity on the further elastomer layer. A further electrode arrangement may be provided in conductive contact with the further elastomer layer, e.g. the further elastomer layer may be sandwiched in between the further electrode arrangement such as a continuous further electrode arrangement or a further electrode matrix arrangement as explained above, which further electrode arrangement may be conductively coupled to a further sensing circuit for determining the temperature of the further elastomer layer as a function of the measured resistivity with the further electrode arrangement. Such temperature information for instance may be used to prevent the ultrasound transducer tiles 100 from overheating, e.g. by disabling or by reducing the power supplied to the transducer array upon the determined temperature exceeding a critical threshold. Alternatively or additionally, such temperature information may be used to extract quality of contact information for the contact between the ultrasound device 10 and the body of the patient, as the temperature of the further elastomer layer typically increases with increasing quality of this contact.

In embodiments of the present invention, the ultrasound device 10 may be an ultrasound probe or the like for use in an ultrasound imaging system or an ultrasound therapy system. For example, such an ultrasound probe may form part of a catheter for invasive imaging or treatment, may form part of a hand-held device for non-invasive imaging or treatment or may form part of a wearable device, e.g. for prolonged treatment of particular area of the body of a patient. Non-limiting examples of such probes include transesophageal echocardiogram (TEE) probes, intravascular probes such as intracardiac echo catheters, and so on.

Figure 4:
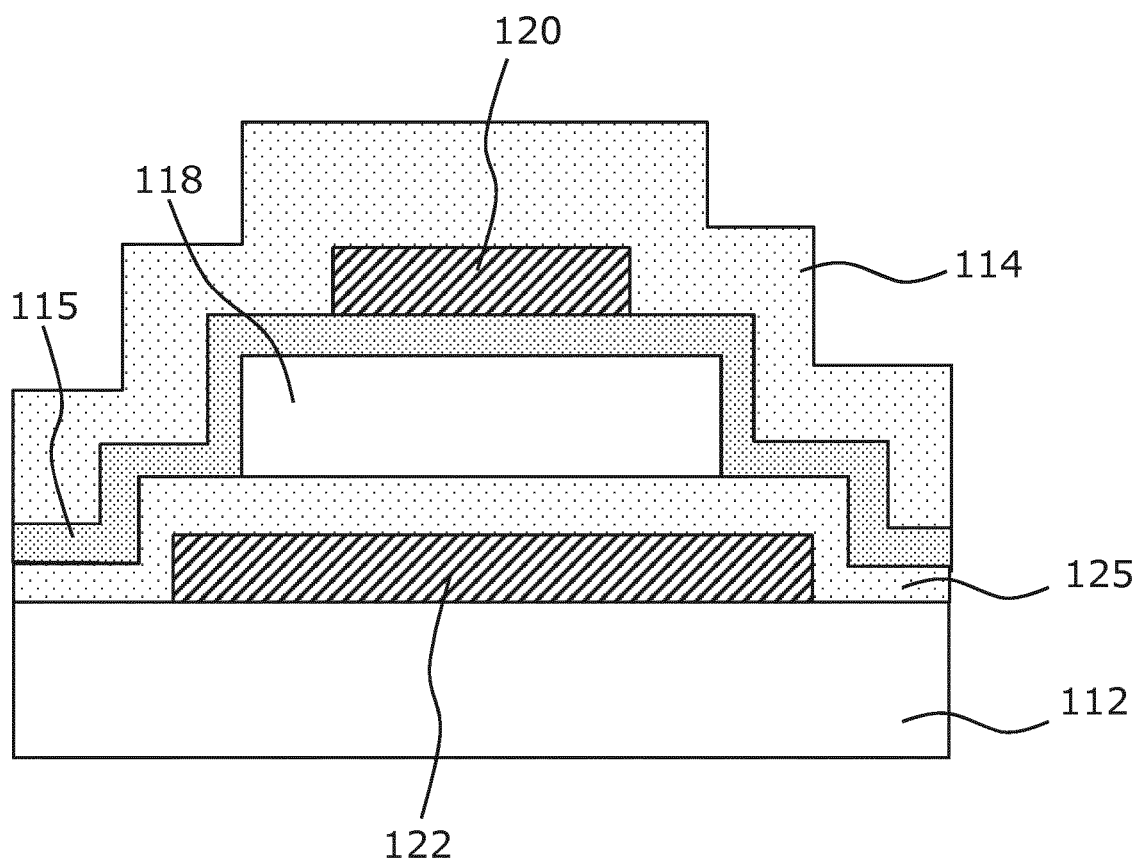
FIG. 4 schematically depicts an example embodiment of a transducer element of an ultrasound device according to embodiments of the present invention.

In preferred embodiments of the present invention, each ultrasound transducer tile 100 comprises one or more CMUT elements. FIG. 4 schematically depicts an example embodiment of a CMUT element. Such a CMUT element typically comprises a membrane or diaphragm 115 suspended above a silicon substrate 112 with a gap or cavity 118 therebetween. A top electrode 120 is located on the diaphragm 114 and moves with the diaphragm 115. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate 112 by way of non-limiting example. Other suitable arrangements, e.g. other electrode shapes and other locations of the bottom electrode 122, e.g. on the substrate layer 112 such that the bottom electrode 122 is directly exposed to the gap 118 or separated from the gap 118 by an electrically insulating layer or film 125 to prevent a short-circuit between the top electrode 120 and the bottom electrode 122, may be contemplated.

In addition, the membrane layer 114 is fixed relative to the top face of the substrate layer 112 and configured and dimensioned so as to define a spherical or cylindrical cavity 118 between the membrane layer 114 and the substrate layer 112. The bottom electrode 122 may be grounded by way of non-limiting example. Other arrangements, e.g. a grounded top electrode 120 or both top electrode 120 and bottom electrode 122 floating are of course equally feasible.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

In an embodiment, the bottom electrode 122 is insulated on its cavity-facing surface with an additional layer (not pictured). A preferred electrically insulating layer is an oxide-nitride-oxide (ONO) dielectric layer formed above the substrate electrode 122 and below the membrane electrode 120 although it should be understood any electrically insulating material may be contemplated for this layer. The ONO-dielectric layer advantageously reduces charge accumulation on the electrodes which leads to device instability and drift and reduction in acoustic output pressure.

An example fabrication of ONO-dielectric layers on a CMUT element is discussed in detail in European patent application EP 2,326,432 A2 by Klootwijk et al., filed Sep. 16, 2008 and entitled "Capacitive micromachined ultra sound transducer." Use of the ONO-dielectric layer is desirable with pre-collapsed CMUTs, which are more susceptible to charge retention than CMUTs operated with suspended membranes. The disclosed components may be fabricated from complementary metal oxide semiconductor (CMOS) compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process.

Suitable CMOS processes are low pressure chemical vapor deposition (LPCVD) and plasma enhanced chemical vapor deposition (PECVD), the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser). In the exemplary embodiment depicted in FIG. 4, the diameter of the cylindrical cavity 118 is larger than the diameter of the circularly configured electrode plate 122. Electrode 120 may have the same outer diameter as the circularly configured electrode plate 122, although such conformance is not required. Thus, in an exemplary implementation of the present invention, the membrane electrode 120 is fixed relative to the top face of the membrane layer 114 so as to align with the electrode plate 122 below.

Figure 5:
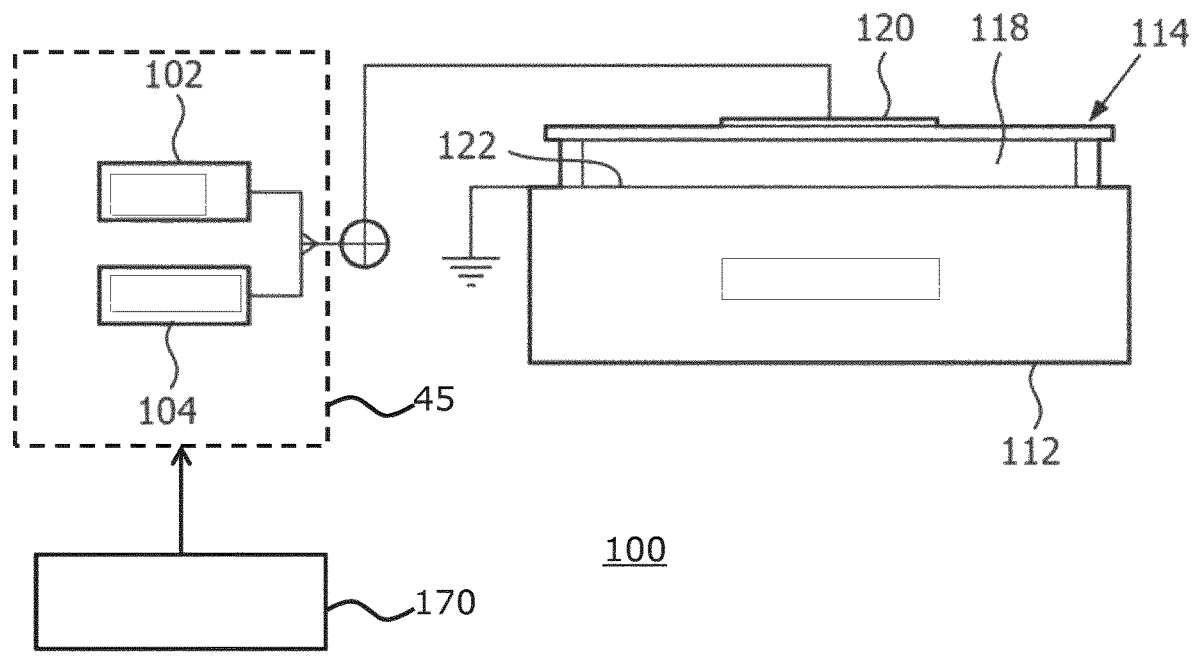
FIG. 5 schematically depicts an aspect of an ultrasound system according to an embodiment.

The electrodes of the CMUT provide the capacitive plates of the device and the gap 118 is the dielectric between the plates of the capacitor. When the diaphragm vibrates, the changing dimension of the dielectric gap between the plates provides a changing capacitance which is sensed as the response of the CMUT to a received acoustic echo. The spacing between the electrodes is controlled by applying a static voltage, e.g. a DC bias voltage, to the electrodes with a power supply 45, as schematically depicted in FIG. 5. The power supply 45 is typically adapted to provide a stimulus to the respective ultrasound transducer tiles 100, e.g. to individual transducer elements of these tiles or by simultaneously addressing the transducer elements of these tiles such that each tile 100 operates as a single transducer element (composed of synchronized CMUT elements).

The power supply 45 may be adapted to operate the transducer elements of the ultrasound device 10 such that the membranes of the transducer elements in case of CMUT elements are to resonate freely. In an alternative embodiment, the power supply 45 may be adapted to operate such CMUT elements such that the respective membranes of the addressed CMUT elements are collapsed onto the substrate 112, i.e. are in collapse mode. To this end, the power supply 45 may comprise a first stage 102 adapted to produce a bias voltage that forces the membranes of selected capacitive micromachined ultrasound transducers into the collapsed mode and a second stage 104 adapted to produce an alternating voltage on top of the bias voltage that forces the membranes in the collapsed mode to resonate. Alternatively, this bias voltage and alternating voltage on top of the bias voltage may be produced by a single stage of the power supply 45.

As is known per se, by applying a static voltage above a certain threshold, the CMUT is forced into a collapsed state in which the membrane 114 collapses onto the substrate 112. This threshold value may depend on the exact design of the CMUT and is defined as the DC bias voltage at which the membrane 114 sticks to (contacts) the cell floor by Vander-Waals force during the application of the bias voltage. The amount (area) of contact between the membrane 114 and the substrate 112 is dependent on the applied bias voltage. Increasing the contact area between the membrane 114 and the substrate 112 causes an increase of the resonance frequency of the membrane 114. This will be explained in more detail with the aid of FIG. 6a, 6b and FIG. 7a, 7b.

Figure 6A:
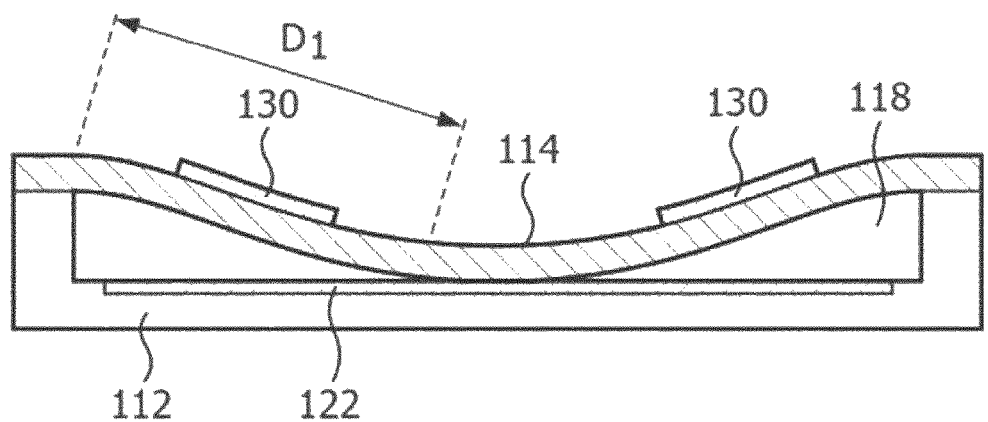
FIGS. 6a, 6b, 7a and 7b schematically depict example modes of operation of the ultrasound system of FIG. 5.
Figure 7A:
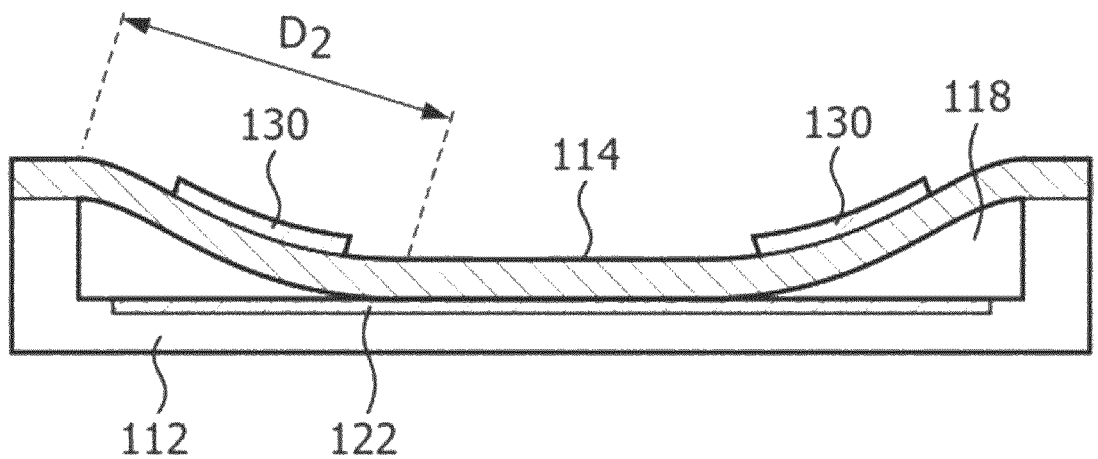

The frequency response of a collapsed mode CMUT may be varied by adjusting the DC bias voltage applied to the CMUT electrodes 130 and 122 after collapse with the power supply 45. As a result, the resonant frequency of the CMUT cell increases as a higher DC bias voltage is applied to the electrodes 130 and 122. The cross-sectional views of FIGS. 6a and 7a illustrate this one-dimensionally by the distances D1 and D2 between the outer support of the membrane 114 and the point where the membrane begins to touch the floor of the cavity 118 (i.e. the substrate 112) in each illustration. It can be seen that the distance D1 is a relatively long distance in FIG. 6a when a relatively low bias voltage is applied, whereas the distance D2 in FIG. 7a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 6a will be lower than the resonant frequency of the CMUT cell in FIG. 7a which is subject to the higher pulldown bias voltage.

Figure 6B:
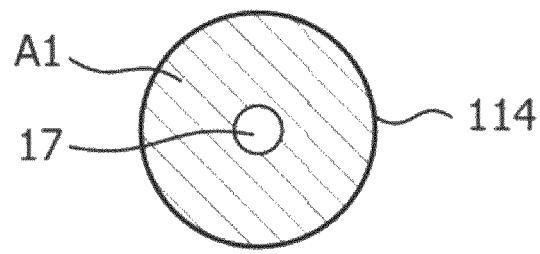
Figure 7B:
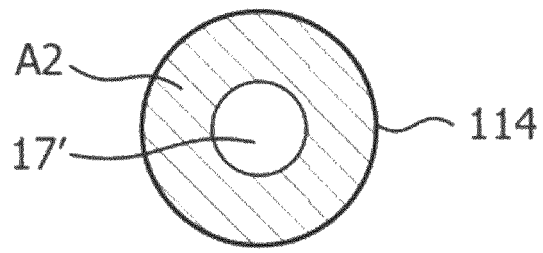

The phenomenon can also be appreciated from the two dimensional illustrations of FIGS. 6b and 7b, as it is in actuality a function of the effective operating area of the CMUT membrane 114. When the membrane 114 just touches the floor of the CMUT as shown in FIG. 6a, the effective vibrating area A1 of the non-contacting (free vibrating) portion of the cell membrane 114 is large as shown in FIG. 6b. The small hole in the center 17 represents the center contact region of the membrane 114. The large area membrane will vibrate at a relatively low frequency. This area 17 is an area of the membrane 114, which is collapsed to the floor of the CMUT. But when the membrane is pulled into deeper collapse by a higher bias voltage as in FIG. 7a, the greater central contact area 17' results in a lesser free vibrating area A2 as shown in FIG. 7b. This lesser area A2 will vibrate at a higher frequency than the larger A1 area. Thus, as the DC bias voltage is decreased the frequency response of the collapsed CMUT decreases, and when the DC bias voltage increases the frequency response of the collapsed CMUT increases.

As shown in FIG. 5, the power supply 45 may be responsive to the sensing circuit 170 (and to the further sensing circuit conductively coupled to a temperature-sensitive further elastomer layer if present in the acoustic window 150). In this embodiment, the sensing circuit 170 may be adapted to generate a warning signal for the power supply 45 in case of a measured piezoelectric resistance of the elastomer layer 153 (and/or measured thermoelectric resistance of the further elastomer layer) being indicative of a substandard contact between the ultrasound device and the patient's body.

The power supply 45 may be adapted to temporarily halt the provision of the respective control signals to the ultrasound transducer tiles 100, e.g. a bias voltage forcing the respective CMUT elements into collapse mode, in response to such a warning signal such that the respective CMUT elements of the transducer array are only forced into collapse mode when a conformal contact of sufficient quality between the ultrasound device 10 and the patient's body is established. In this manner, the lifetime of the CMUT elements may be extended by only operating the CMUT elements when the quality of the contact between the ultrasound device 10 and the patient's body facilitates effective treatment or imaging. Alternatively, the sensing circuit 170 may provide raw sensor data to the power supply 45, with the power supply 45 comprising a processor or the like adapted to process the raw sensor data and to derive an indication of the quality of contact between the ultrasound device 10 and the patient's body from the processed raw sensor data. The power supply 45 may restore the provision of the respective control signals to the ultrasound transducer tiles 100 upon receiving an indication that the contact between the ultrasound device 10 and the patient's body is of sufficient quality to restore operation of the ultrasound device 10. Similarly, the power supply 45 may be adapted to temporarily halt the provision of the respective control signals to the ultrasound transducer tiles 100, e.g. a bias voltage forcing the respective CMUT elements into collapse mode, in response to the further electrode arrangement associated with the temperature-sensitive further elastomer layer providing an indication that the temperature in the further elastomer layer has exceeded a critical threshold, i.e. the ultrasound device 10 is at risk of overheating.

Alternatively, the power supply 45 may be adapted to temporarily reduce the power supplied to the ultrasound transducer tiles 100 in response to an indication of a substandard conformal contact between the ultrasound device 10 and the patient's body and/or an indication of the ultrasound device 10 being at risk of overheating.

Figure 8:
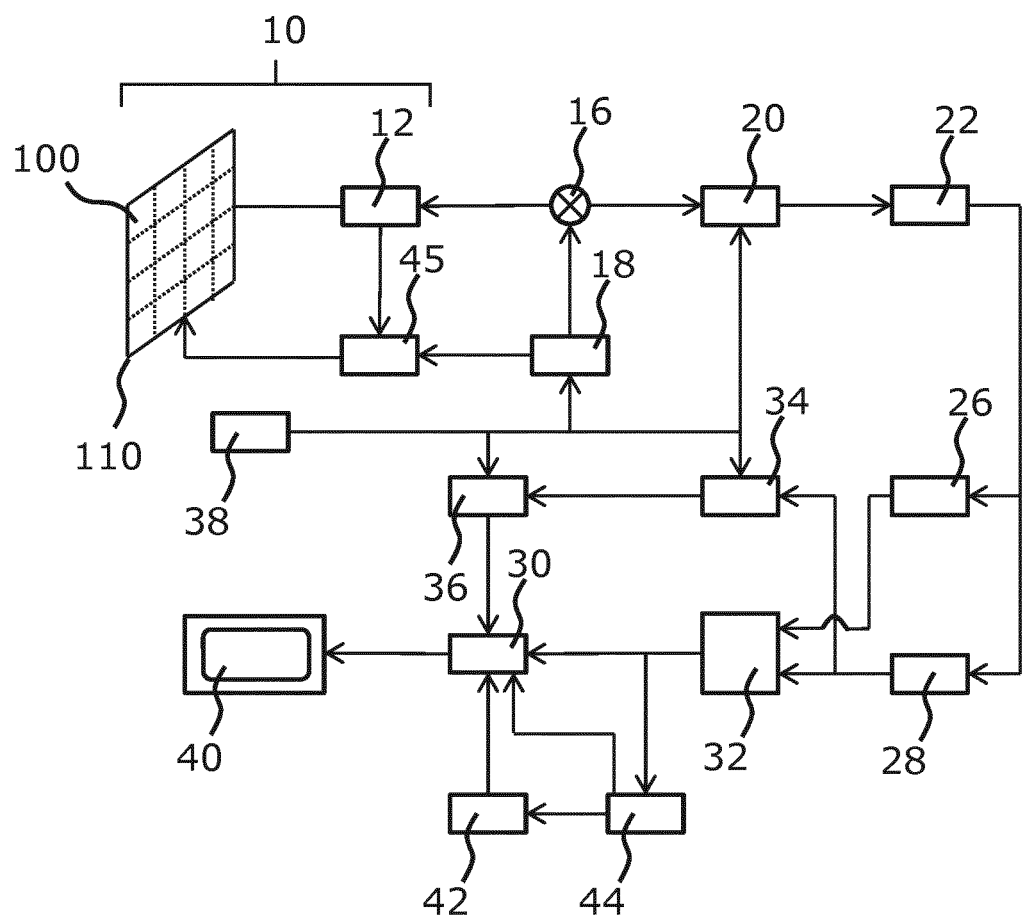
FIG. 8 schematically depicts a circuit diagram of an ultrasound system according to an embodiment.

The ultrasound device 10 and the power supply 45 may form part of an ultrasound system such as an ultrasonic diagnostic imaging system or an ultrasonic therapy system. An example embodiment of an ultrasonic diagnostic imaging system 1 is schematically depicted in block diagram form in FIG. 8. A transducer array 110 comprising the ultrasound transducer tiles 100 is provided in an ultrasound device 10 for transmitting ultrasonic waves and receiving echo information. The transducer array 110 may be a one- or a two-dimensional array of transducer elements, e.g. tiles 100, capable of scanning in a 2D plane or in three dimensions for 3D imaging.

The transducer array 110 is coupled to a microbeam former 12 in the probe 10 which controls transmission and reception of signals by the array cells, e.g. CMUT cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial wire, to a transmit/receive (T/R) switch 16 which switches between transmission and reception modes and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control the aforementioned voltage source 45 for the transducer array 110. For instance, the voltage source 45 sets the DC and AC bias voltage(s) that are applied to the CMUT cells 100 of a CMUT array 110, e.g. to drive the CMUT cells into collapse mode as explained above.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of transducer cells, e.g. from tiles 100. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

Moreover, in case of an ultrasonic therapy system, there obviously is no need for the system to be able to receive and process pulse echoes, such that it will be immediately apparent to the skilled person that the above embodiment of an ultrasonic diagnostic imaging system may be adapted to form an ultrasonic therapy system by omission of those system components that are required for the reception of processing of such pulse echoes.

Figure 9:
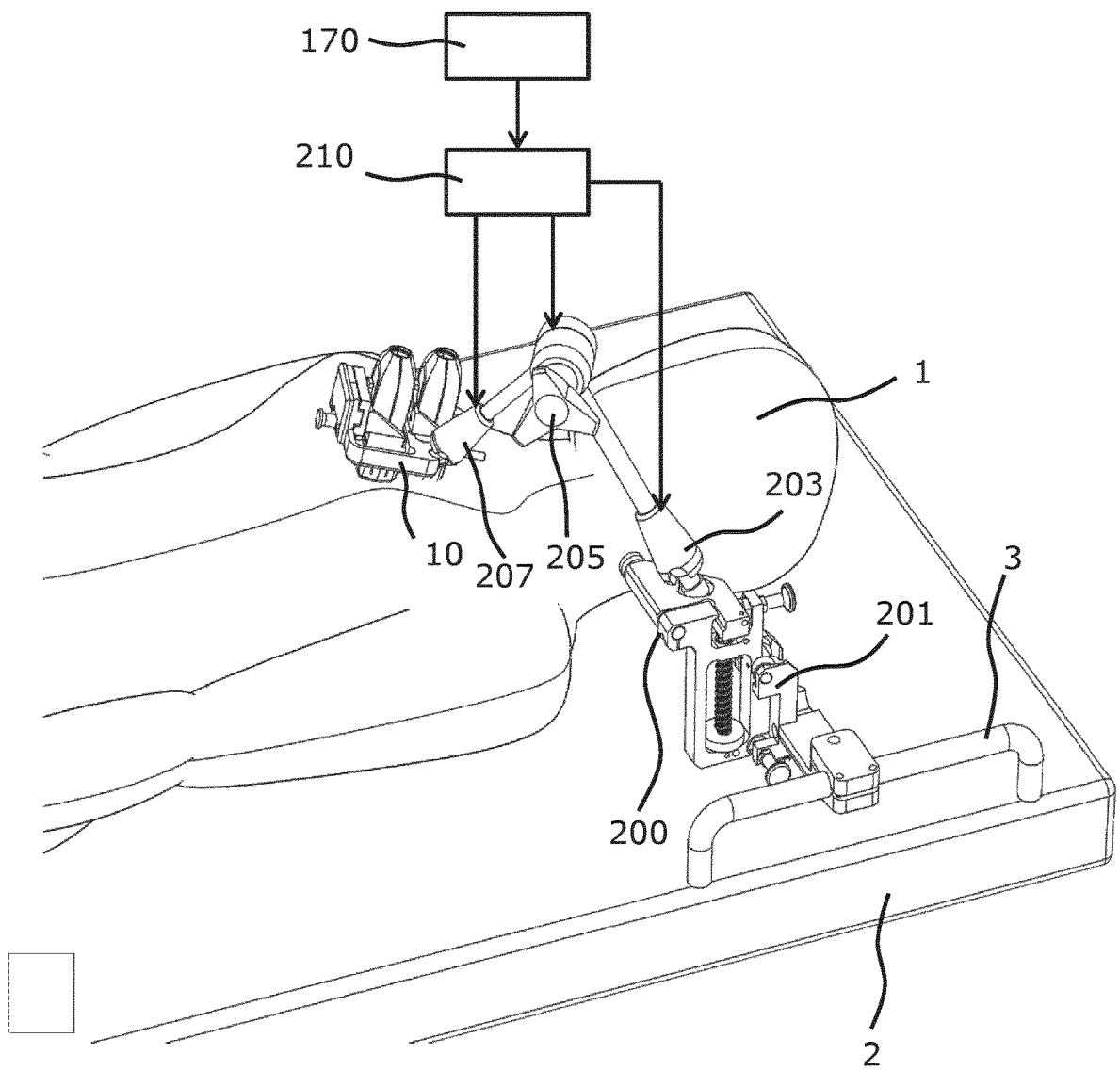
FIG. 9 schematically depicts an ultrasound arrangement according to an embodiment.

FIG. 9 schematically depicts an example embodiment of an ultrasound arrangement of the present invention. The ultrasound arrangement comprises a holder 200 for holding the ultrasound device 10, which holder comprises one or more actuators that can be controlled by a controller 210 to adjust the orientation of the ultrasound device 10 in the holder 200. For example, the holder 200 may be an arm mountable to a treatment table 2, e.g. to a grip 3 on the upper surface of the treatment table 2 for supporting a patient 1. The arm may comprise a mounting member 201, e.g. a clamp or the like, for affixing the arm to the treatment table 2. The arm may comprise one or more actuated hinges 203, 205, 207 under control of the controller 210, which hinges may be actuated to change the orientation of the ultrasound device 10 in response to a control signal provided by the controller 210. The controller 210 may be responsive to the sensing circuit 170 and may be adapted to systematically adjust the orientation of the ultrasound device 10 on the patient's body until the sensing circuit 170 provides an indication of a good-quality contact between the ultrasound device 10 and the patient's body. In other words, the sensing circuit 170 may provide a feedback signal for the controller 210, which may be used by the controller 210 to establish the desired high-quality contact between the ultrasound device 10 and the patient 1. The controller 210 may be further adapted to periodically alter the orientation of the ultrasound device 10 relative to the patient's body in response to the sensing circuit 170 providing an indication of the change (deterioration) in the quality of contact between the ultrasound device 10 and the patient's body as obtained from a measured change in the piezoelectric resistivity of the elastomer layer 153 as previously explained in order to restore to the desired quality of contact between the ultrasound device and the patient 1. A similar arrangement may be used to achieve a sufficient acoustic contact at minimal pressure, e.g. for an ultrasound arrangement used for esophageal echography where the sensing circuit 170 provides an indication of the amount of pressure provided to the esophageal wall.

In an embodiment, in which the ultrasound device 10 comprises a patterned electrode arrangement 160, the controller 210 may be adapted to control the actuated hinges 203, 205, 207 in response to a pressure map corresponding to the respective pressures in the individual portions of the elastomer layer 153 as sensed with the electrode arrangement 160. For example, the controller 210 may be adapted to control the actuated hinges 203, 205, 207 to minimize pressure gradients in the pressure map, i.e. to even out the pressure across the elastomer layer 153. The control signals applied to the actuated hinges 203, 205, 207 may be derived from such pressure gradients.

Other embodiments in which such feedback from the sensing circuit 170 is used to adjust the orientation of the ultrasound device 10 may be contemplated. For example, the ultrasound device 10 may comprise integrated actuators arranged to alter the orientation of individual transducer tiles 100 in response to the feedback information provided by the sensing circuit 170. This embodiment for example is particularly advantageous in combination with the patterned elastomer layer 153 as schematically depicted in FIG. 3, where each elastomer layer portion may be aligned with and dimensioned to correspond to an individual transducer tile 100, such that a quality of contact for each individual transducer tile 100 may be controlled by altering the orientation of the individual transducer tile 100 with the integrated actuator in response to feedback information provided by the sensing circuit 170 specific to that particular individual transducer tile.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound device comprising:
a transducer arrangement;
an acoustically transmissive window over said transducer arrangement, said acoustically transmissive window comprising an elastomer layer having electrically conductive particles dispersed in the elastomer layer such that an area of the elastomer layer over the transducer arrangement has a pressure-sensitive electrical conductivity, wherein the pressure-sensitive electrical conductivity corresponds to a pressure applied to the area of the elastomer layer over the transducer arrangement; and
an electrode arrangement coupled to said elastomer layer and adapted to measure said pressure-sensitive electrical conductivity,
wherein the transducer arrangement is adapted to generate ultrasound waves in a subject to be exposed to the ultrasound waves, and
wherein the electrically conductive particles have a maximum diameter depending on a minimum wavelength associated with the ultrasound waves such that the ultrasound waves propagate through the area of the elastomer layer over the transducer arrangement without being reflected or scattered by the electrically conductive particles dispered in the area of the elastomer layer over the transducer arrangement.

2. The ultrasound device of claim 1, wherein an acoustic impedance of the elastomer layer is in a range of 1.3-3.0 MRayls.

3. The ultrasound device of claim 1, wherein the elastomer is a polyolefin, a diene polymer or a polysiloxane, a co-polymer or block-copolymer comprising a polyolefin, a diene polymer or a polysiloxane or a blend thereof.

4. The ultrasound device of claim 1, wherein the electrically conductive particles comprise at least one of carbon particles, carbon composite particles, ceramic particles, metal particles, metal alloy particles, composite metal particles or conductive metal oxide particles.

5. The ultrasound device of claim 1, wherein a volume of the electrically conductive particles in the elastomer layer is at least 15% by volume based on a total volume of the elastomer layer.

6. The ultrasound device of claim 1, wherein the elastomer layer has a thickness in a range of 10-200 μm.

7. The ultrasound device of claim 1, wherein the elastomer layer comprises a mixture of electrically conductive particles and electrically non-conductive particles dispersed in the elastomer layer.

8. The ultrasound device of claim 1, wherein the elastomer layer is sandwiched in between electrodes of the electrode arrangement.

9. The ultrasound device of claim 8, wherein the electrode arrangement comprises an electrode matrix arranged to measure the pressure-sensitive electrical conductivity of individual portions of the elastomer layer.

10. The ultrasound device of claim 1, wherein the acoustically transmissive window comprises a further elastomer layer having further electrically conductive particles dispersed therein, the further elastomer layer having a temperature-sensitive electrical conductivity, the ultrasound device further comprising a further electrode arrangement coupled to said further elastomer layer adapted to measure said temperature-sensitive electrical conductivity.

11. An ultrasound system comprising the ultrasound device of claim 1, the ultrasound system further comprising a power supply adapted to drive the transducer arrangement of the ultrasound device, wherein the power supply is responsive to the electrode arrangement and adapted to disable the transducer arrangement upon a signal from the electrode arrangement indicative of a change in resistivity of the elastomer layer.

12. The ultrasound system of claim 11,
wherein the transducer arrangement comprises a plurality of capacitive micromachined ultrasonic transducers, each transducer comprising:
a membrane over a substrate, the membrane and the substrate delimiting a cavity;
a first electrode on the substrate separated from the cavity by a first electrically insulating layer; and
a second electrode supported by the membrane opposite the first electrode,
wherein the power supply is adapted to provide the first electrodes and the second electrodes of the respective capacitive micromachined ultrasound transducers with:
a bias voltage that forces the membranes of selected capacitive micromachined ultrasound transducers into a collapsed mode; and
an alternating voltage on top of the bias voltage that forces the membranes in the collapsed mode to resonate.

13. An ultrasound arrangement comprising the ultrasound device of claim 1 and a holder adapted to hold the ultrasound device in an orientation against a body surface to be exposed to ultrasound waves generated with the ultrasound device, the holder comprising an actuator arrangement for adjusting the orientation of the ultrasound device and a controller adapted to control the actuator arrangement, the controller being responsive to a signal provided by the electrode arrangement indicative of a change in resistivity of the elastomer layer.

14. The ultrasound arrangement of claim 13, wherein the change in resistivity of the elastomer layer is indicative of a quality of contact between the ultrasound device and the subject, and wherein the control of the actuator arrangement affects the quality of contact between the ultrasound device and the subject.

15. The ultrasound device of claim 1, wherein the maximum diameter of the electrically conductive particles minimizes acoustic scattering of the ultrasound waves caused by the electrically conductive particles.

16. The ultrasound device of claim 1, wherein the electrically conductive particles of the elastomer layer further include:
   an electrical conductivity such that the pressure-sensitive electrical conductivity of the elastomer layer is above a threshold value when the elastomer layer is in a compressed state, and
   a density such that an acoustic impedance of the elastomer layer in the compressed state is matched to at least one of an acoustic impedance of the subject or an acoustic impedance of the transducer arrangement.

17. The ultrasound device of claim 12, wherein the power supply is adapted to halt the bias voltage upon a signal from the electrode arrangement indicative of a change in resistivity of the elastomer layer the membranes of selected capacitive micromachined ultrasound transducers are not forced into the collapsed mode.

18. The ultrasound device of claim 1, wherein the maximum diameter of the electrically conductive particles is less than 10% of the minimum wavelength associated with the ultrasound waves.

* * * * *